(12) United States Patent
Peyman (10) Patent No.: US 11,730,890 B1
(45) Date of Patent: Aug. 22, 2023

(54) PLUNGERLESS ASPIRATION AND/OR INJECTION DEVICE AND METHOD USING THE SAME

(71) Applicant: Gholam A. Peyman, Sun City, AZ (US)

(72) Inventor: Gholam A. Peyman, Sun City, AZ (US)

(*) Notice: Subject to any disclaimer, the term of this patent is extended or adjusted under 35 U.S.C. 154(b) by 392 days.

(21) Appl. No.: 17/144,075

(22) Filed: Jan. 7, 2021

Related U.S. Application Data (60) Provisional application No. 62/958,101, filed on Jan. 7, 2020.

(51) Int. Cl.
| | |
|---|---|
| *A61M 5/178* | (2006.01) |
| *A61M 5/00* | (2006.01) |
| *A61M 5/28* | (2006.01) |
| *A61B 10/00* | (2006.01) |
| *A61M 5/31* | (2006.01) |

(52) U.S. Cl.
CPC ......... *A61M 5/282* (2013.01); *A61B 10/0045* (2013.01); *A61M 5/31* (2013.01); *A61M 2005/3112* (2013.01); *A61M 2005/3132* (2013.01); *A61M 2205/0205* (2013.01)

(58) Field of Classification Search
CPC ............ A61M 2210/0612; A61M 1/68; A61M 1/682; A61M 1/684; A61M 2005/3132; A61M 2005/3112; A61M 5/32; A61M 5/282; A61B 10/0045
See application file for complete search history.

(56) References Cited

U.S. PATENT DOCUMENTS

| | | | | |
|---|---|---|---|---|
| 2,618,263 | A * | 11/1952 | Lakso ................... | A61M 5/282 604/204 |
| 2,771,879 | A * | 11/1956 | Salisbury, Jr. ........ | A61M 5/282 604/900 |
| 3,776,238 | A | 12/1973 | Peyman et al. | |
| 4,428,748 | A | 1/1984 | Peyman et al. | |
| 4,548,601 | A * | 10/1985 | Lary ...................... | A61M 5/282 604/212 |
| 4,955,871 | A * | 9/1990 | Thomas ................ | A61M 5/282 222/215 |
| 5,217,480 | A * | 6/1993 | Haber ................ | A61B 5/15113 D24/112 |

(Continued)

FOREIGN PATENT DOCUMENTS

| | | | | |
|---|---|---|---|---|
| DE | 19537271 A1 * | 4/1997 | ........... | A61B 5/0215 |
| DE | 10032937 A1 * | 1/2001 | ............ | A61M 5/282 |

*Primary Examiner* — Rebecca E Eisenberg
(74) *Attorney, Agent, or Firm* — The Law Office of Patrick F. O'Reilly III, LLC (57) ABSTRACT

A plungerless aspiration and/or injection device and a method of using the same are disclosed herein. The plungerless aspiration and/or injection device includes a housing; a needle portion disposed in the housing, the needle portion configured to be selectively retracted and extended by a user, the needle potion comprising a needle tip configured to be inserted into tissue of a patient for aspiration, injection, and/or implantation; and a bulb portion disposed in the housing, the bulb portion defining a fluid containing cavity that is fluidly coupled to the needle portion, and the bulb portion being elastically deformable so that the user is able to perform the aspiration, the injection, and/or the implantation on the patient by manipulating the bulb portion.

23 Claims, 6 Drawing Sheets

(56) References Cited

U.S. PATENT DOCUMENTS

| | | |
|---|---|---|
| 5,487,725 A | 1/1996 | Peyman |
| 5,547,473 A | 8/1996 | Peyman |
| 6,432,078 B1 | 8/2002 | Peyman |
| 2005/0101967 A1* | 5/2005 | Weber .................. A61F 9/0017 |
| | | 606/107 |
| 2005/0251105 A1 | 11/2005 | Peyman |
| 2009/0171311 A1* | 7/2009 | Genosar ................ A61M 5/282 |
| | | 604/411 |
| 2010/0047914 A1 | 2/2010 | Peyman et al. |
| 2012/0265149 A1* | 10/2012 | Lerner ................ A61M 5/2033 |
| | | 604/190 |
| 2013/0345669 A1* | 12/2013 | Ferreri .................. B65D 35/28 |
| | | 604/125 |

* cited by examiner

PLUNGERLESS ASPIRATION AND/OR INJECTION DEVICE AND METHOD USING THE SAME

CROSS-REFERENCE TO RELATED APPLICATIONS

This patent application claims priority to, and incorporates by reference in its entirety, U.S. Provisional Patent Application No. 62/958,101, entitled "Plungerless Aspiration And Injection Device And Method Using The Same", filed on Jan. 7, 2020.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to a plungerless aspiration and/or injection device and a method using the same. More particularly, the invention relates to a plungerless aspiration and/or injection device for aspirating a liquid biopsy or injecting a medication in bodily tissue.

2. Background

Despite progress in blood liquid biopsy, the aqueous and vitreous fluid is seldom used for diagnostic purposes except in cases of endophthalmitis. However, the aqueous, vitreous, and subretinal fluid contains many molecules that could provide information about the health of the retina, choroid, optic nerve, or the health of the lens or the trabecular meshwork of the eye.

At present, most medications are delivered to the eye by topical drops, or injection using known standard syringes. The topical application has the disadvantage of being washed from the surface of the eye rapidly by the flow of the tear film. The injected medication stays in the tissue a longer time. The syringes have been long used for either injection of medication or aspiration of fluid including a liquid biopsy from the eye or the veins, arteries, or body cavities.

The syringe is composed of a circular tubular body in which a plunger moves forward by the thumb of the user or the plunger is withdrawn using thumb and index fingers. A needle is placed on the syringe to penetrate tissue and deliver medication. The needle can be mounted on the syringe or turned in or out via a luer lock to the syringe.

The plunger also can be connected to an automated air pressure capsule for injection of mediation only. When activated, it forces the tip of the needle and medication, thereby injecting the medication in the tissue.

The use of a syringe for injection is in general cumbersome. It is hard to control the degree of the needle penetration in the tissue with the thumb, and aspiration requires the use of both hands to have the syringe stable in place. While one can predetermine the length of the needle that enters a cavity, it is still difficult to withdraw fluid without the use of both hands, one for stabilizing the syringe and another for withdrawing a liquid biopsy.

In general, the automated systems of injection for withdrawing fluid work like "one size fits all", but fall short in practice.

Therefore, there is a need for a plungerless aspiration and/or injection device for facilitating the aspiration of a liquid biopsy or the injection of a medication in bodily tissue. In addition, because of the sensitive structure of the eye, there is a need for a more refined aspiration of the liquid biopsy or injection of the medication in a corneal pocket created during refractive surgery, or in the small anterior chamber, under the conjunctiva, in the suprachoroidal space, or for the sub-retinal injection of a very small volume of medication.

BRIEF SUMMARY OF EMBODIMENTS OF THE INVENTION

Accordingly, the present invention is directed to a plungerless aspiration and/or injection device and a method using the same that substantially obviates one or more problems resulting from the limitations and deficiencies of the related art.

In accordance with one or more embodiments of the present invention, there is provided a plungerless aspiration and/or injection device that includes a housing; a needle portion disposed in the housing, the needle portion configured to be selectively retracted and extended by a user, the needle potion comprising a needle tip configured to be inserted into tissue of a patient for aspiration, injection, and/or implantation; and a bulb portion disposed in the housing, the bulb portion defining a fluid containing cavity that is fluidly coupled to the needle portion, and the bulb portion being elastically deformable so that the user is able to perform the aspiration, the injection, and/or the implantation on the patient by manipulating the bulb portion.

In a further embodiment of the present invention, the plungerless aspiration and/or injection device further comprises a knob for manipulating the needle portion, the knob being slidably disposed within a slot of the housing. In this further embodiment, when the knob is moved in a first direction by the user, the needle portion is retracted into the housing; and, when the knob is moved in a second direction by the user, the needle portion is extended out of the housing, the second direction being opposite to the first direction.

In yet a further embodiment, the bulb portion is connected to the needle portion such that the bulb portion is displaced with the needle portion when the knob is moved in the first direction or second direction by the user.

In still a further embodiment, the housing comprises elastically deformable forked blades disposed over the bulb, the elastically deformable forked blades configured to be depressed by the user between a thumb and index finger of the user so as to more controllably regulate a flow of fluid out of, or into the needle tip.

In yet a further embodiment, the housing further comprises a plate member with a plurality of grooves disposed therein, and at least one of the elastically deformable forked blades is configured to engage with respective ones of the plurality of grooves in the plate member so as to enable graduated amounts of the fluid to be discharged from the plungerless aspiration and/or injection device.

In still a further embodiment, the needle portion has a 19 gauge to 44 gauge needle diameter.

In yet a further embodiment, the needle portion has a diameter between approximately 0.001 millimeters and approximately 2.0 millimeters, or more than 2.0 millimeters.

In still a further embodiment, the needle portion has a needle length between approximately 1 millimeters and approximately 100 millimeters, or more than 100 millimeters.

In yet a further embodiment, the bulb portion is formed from a compressible silicone, rubber, or other elastic polymer.

In still a further embodiment, the housing comprises a dull tip end so that, when the needle portion is retracted in the housing, the plungerless aspiration and/or injection device is able to be moved over a surface of the tissue of the patient to select a desired penetration location without scratching or cutting the surface of the tissue.

In yet a further embodiment, the housing comprises a graded flexible guard that indicates the amount of the fluid or medication that is injected in a body cavity.

In accordance with one or more other embodiments of the present invention, there is provided a method of using a plungerless aspiration and/or injection device. The method comprises the steps of: (i) providing a plungerless aspiration and/or injection device that includes a housing; a needle portion disposed in the housing, the needle portion configured to be selectively retracted and extended by a user, the needle potion comprising a needle tip configured to be inserted into tissue of a patient for aspiration, injection, and/or implantation; and a bulb portion disposed in the housing, the bulb portion defining a fluid containing cavity that is fluidly coupled to the needle portion, and the bulb portion being elastically deformable so that the user is able to perform the aspiration, the injection, and/or the implantation on the patient by manipulating the bulb portion; (ii) positioning the housing of the plungerless aspiration and/or injection device over a body portion of the patient; (iii) displacing the needle portion of the plungerless aspiration and/or injection device outward from the housing such that the needle tip penetrates the tissue of the patient; and (iv) compressing the bulb portion of the plungerless aspiration and/or injection device to either inject a fluid or implant into the tissue of the patient, or to aspirate a fluid biopsy from a body cavity or the tissue of the patient.

In a further embodiment of the present invention, the method further comprises the step of filling the fluid containing cavity of the bulb portion with a fluid, a medication, an implant, proteins, cells, or genetic components; and the step of compressing the bulb portion further comprises compressing the bulb portion to inject the fluid, the medication, the implant, the proteins, the cells, or the genetic components into the tissue, circulation, or body cavity of the patient.

In yet a further embodiment, the step of filling the fluid containing cavity of the bulb portion further comprises filling the fluid containing cavity with pluralities of functionalized antibody-coated nanoparticles conjugated with checkpoint inhibitors, oncolytic viruses, viral-like particles, immune stimulators, venoms, antivirals, antibiotics, antifungals, antineoplastic medications, inflammatory cell pathway inhibitors, steroids, anti-glaucoma medication and/or anti-VEGFs to be injected inside a tumor or circulation of the patient so as to release checkpoint inhibitors, oncolytic viruses, viral-like particles, immune stimulators, venoms, antivirals, antibiotics, antifungals, antineoplastic medications, inflammatory cell pathway inhibitors, steroids, anti-glaucoma medication and/or anti-VEGFs. The checkpoint inhibitors, oncolytic viruses, viral-like particles, immune stimulators, venoms, antivirals, antibiotics, antifungals, antineoplastic medications, inflammatory cell pathway inhibitors, steroids, anti-glaucoma medication and/or anti-VEGFs may also be provided in a flexible or rigid implant that is injected inside the eye, retina, cornea, choroid, a tumor or circulation of the patient, intramuscularly, subcutaneously, or under the mucosa. In addition, any medication may be provided in suspension in a solution or a solvent such as semifluorinated alkane, or perfluorocarbon liquids and administered by injection, as drops, or a spray.

In still a further embodiment, the checkpoint inhibitors, oncolytic viruses, viral-like particles, immune stimulators, and/or venoms conjugated with the functionalized antibody-coated nanoparticles are released in response to application of external energy, the external energy selected from the group consisting of laser, alternating magnetic field, a focused ultrasound, microwaves, and/or combinations thereof. In one embodiment, the medication is a photosensitizer, such as riboflavin or methylene blue, etc.

In yet a further embodiment, the step of filling the fluid containing cavity of the bulb portion further comprises filling the fluid containing cavity with an emulsion containing nanoparticles or microparticles, solid lipid particles, gold magnetic nanoparticles or microparticles, gold non-magnetic nanoparticles or microparticles, liposomes, micelles, and/or dendrimers in a fluid. In this further embodiment, the microparticles may be up to the size of one millimeter or more.

In still a further embodiment, the step of filling the fluid containing cavity of the bulb portion further comprises filling the fluid containing cavity with a viscoelastic material containing a medication and/or a photosensitizer that is activated using ultraviolet radiation or another type of radiation to crosslink proteins in the tissue of the patient.

In yet a further embodiment, the photosensitizer is selected from the group consisting of riboflavin, porphyrin derivatives, indium, platinum, rhodium plus albumin, eosin, rose Bengal, phthalocyanines, carotenoids, and/or combinations thereof.

In still a further embodiment, the step of filling the fluid containing cavity of the bulb portion further comprises filling the fluid containing cavity with predetermined non-toxic doses of a medication selected from the group consisting of antibiotics, antivirals, anti-parasites, anti-fungals, antivirals, low molecular weight heparin, hyaluronic acid, and/or combinations thereof in a solution or emulsion of nanoparticles or microparticles for slow release of the medication. In this further embodiment, the plungerless aspiration and/or injection device is disposable.

In yet a further embodiment, the step of compressing the bulb portion further comprises compressing the bulb portion to aspirate the fluid biopsy from the body cavity or the tissue of the patient for subsequent analysis.

In still a further embodiment, the method further comprises the step of creating a small hole in an outer wall of the bulb portion to aspirate the fluid biopsy from the body cavity or the tissue of the patient through the needle portion, to the bulb portion, and then to outside the plungerless aspiration and/or injection device where the fluid biopsy is collected, so that the plungerless aspiration and/or injection device is able to be used as a passive biopsy collection system, or the bulb can be filled with a medication, e.g., initially filled or the medication injected in it with a fine needle which is self-sealing for active administration of the medication or withdrawal.

In yet a further embodiment, the plungerless aspiration and/or injection device is configured for a single use on a patient; and the method further comprises the step of disposing of the plungerless aspiration and/or injection device after injecting the fluid or an implant into the tissue of the patient, or aspirating the fluid biopsy from the body cavity or the tissue of the patient.

In still a further embodiment, the method further comprises the steps of inserting the needle tip of the needle portion of the plungerless aspiration and/or injection device inside corneal tissue after femtosecond laser application or a Small Incision Lenticule Extraction procedure; and displacing the needle tip of the needle portion inside the corneal tissue so as to dissect bridges of the corneal tissue after the femtosecond laser application or the Small Incision Lenticule Extraction procedure.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same elements are always denoted using the same reference characters so that, as a general rule, they will only be described once.

DETAILED DESCRIPTION OF EMBODIMENTS OF THE INVENTION

In one embodiment, there is a need for a simplified system that can be easily controlled by thumb and index fingers for injection of fluid or implantation of small sized implants, for example, drug delivery of polymeric nano- and microparticulates or injecting a medication in solution or as emulsion or withdrawing a precise amount of fluid without moving the instrument that could damage the wall of the cavity, such as an artery or vein or the wall of the body cavity, such as the anterior chamber damaging the cornea, lens, or the iris of the eye and/or the vitreous cavity without damaging the retina, etc. (refer to FIGS. 1A-3H).

In one embodiment, the instrument 10 is composed of a housing where its front end covers a movable needle 12 and its back is like a flexible fork 20 or spatula-like extension covering an elongated semi-elastic compressible, silicone bulb reservoir 18 made of silicone or the like, rubber, or elastic polymer (see FIGS. 1A-1E).

Figure 1A:
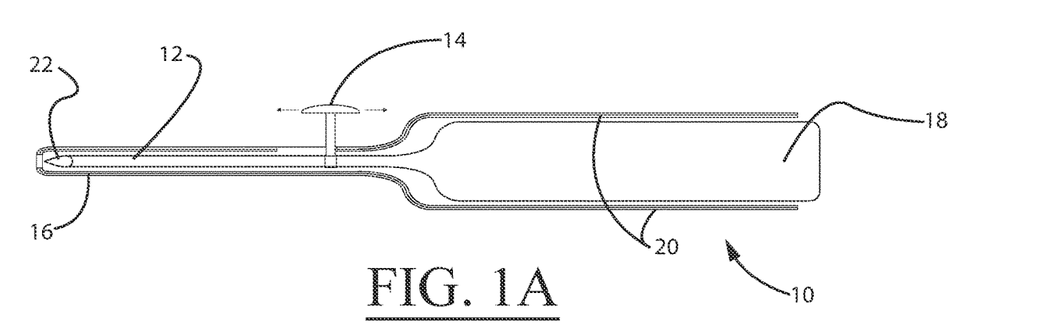
FIG. 1A is a side cross-sectional view of a plungerless aspiration and/or injection device, according to an illustrative embodiment of the invention, wherein the needle of the device is in a retracted position.
Figure 1B:
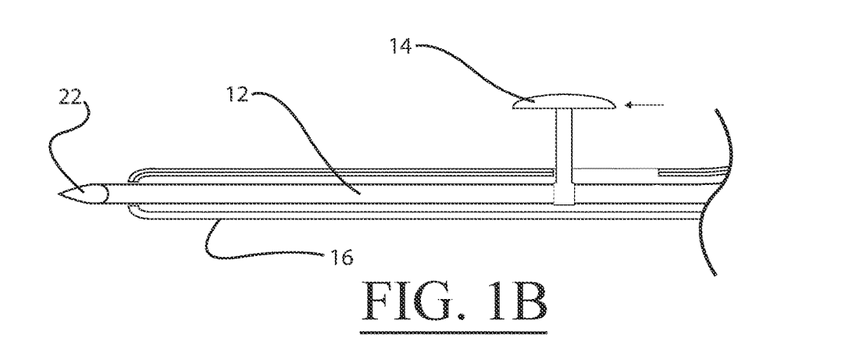
FIG. 1B is a partial side cross-sectional view of a distal end of the plungerless aspiration and/or injection device of FIG. 1A, wherein the needle of the device is in an extended, exposed position.
Figure 1C:
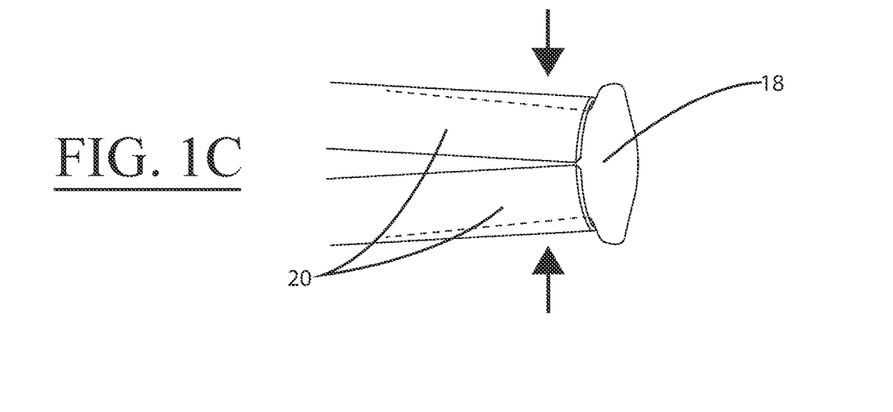
FIG. 1C is a partial side cross-sectional view of a proximal end of the plungerless aspiration and/or injection device of FIG. 1A, wherein the bulb and the fork of the device are illustrated in a compressed state.

In particular, as shown in the illustrative embodiment of FIGS. 1A-1C, the plungerless aspiration and/or injection device 10 comprises a housing 16; a needle portion 12 disposed in the housing 16, the needle portion 12 configured to be selectively retracted and extended by a user, the needle portion 12 comprising a needle tip 22 configured to be inserted into tissue of a patient for aspiration, injection, and/or implantation; and a bulb portion 18 disposed in the housing 16, the bulb portion 18 defining a fluid containing cavity that is fluidly coupled to the needle portion 12, and the bulb portion 18 being elastically deformable so that the user is able to perform the aspiration, the injection, and/or the implantation on the patient by manipulating the bulb portion 18.

Referring again to FIGS. 1A-1C, it can be seen that, in the illustrative embodiment, the plungerless aspiration and/or injection device 10 further comprising a knob 14 for manipulating the needle portion 12, the knob 14 being slidably disposed within a slot of the housing 16. When the knob 14 is moved in a first direction by the user, the needle portion 12 is retracted into the housing 16. Conversely, when the knob 14 is moved in a second, opposite direction by the user, the needle portion 12 is extended out of the housing 16. In the illustrative embodiment, the bulb portion 18 is connected to the needle portion 12 such that the bulb portion 18 is displaced with the needle portion 12 when the knob 14 is moved in the first direction or second direction by the user.

In the illustrative embodiment, as best shown in FIG. 1C, the housing 16 comprises elastically deformable forked blades 20 disposed over the bulb 18, the elastically deformable forked blades 20 configured to be depressed by the user between a thumb and index finger of the user so as to more controllably regulate a flow of fluid out of, or into the needle tip 22. The forked blades 20 may be spring-loaded to return to their undepressed state after being depressed by the user.

Figure 2A:
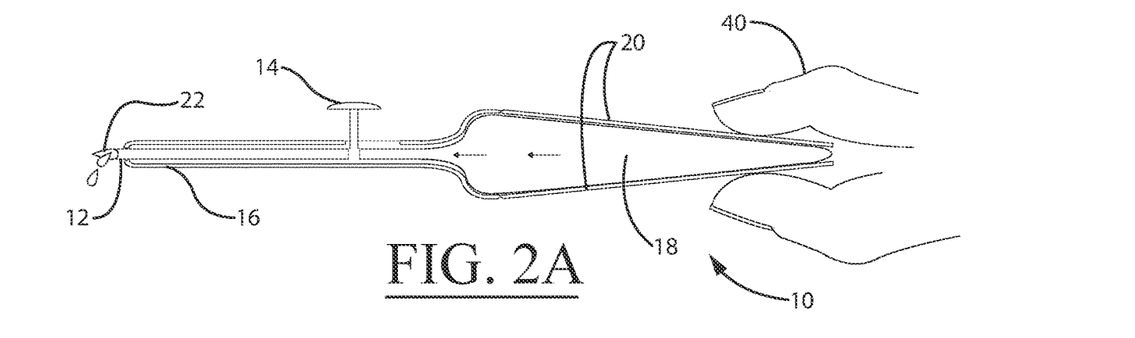
FIG. 2A is a side cross-sectional view of a plungerless aspiration and/or injection device, according to an illustrative embodiment of the invention, wherein the manner in which the device is used for injection is illustrated.
Figure 2B:
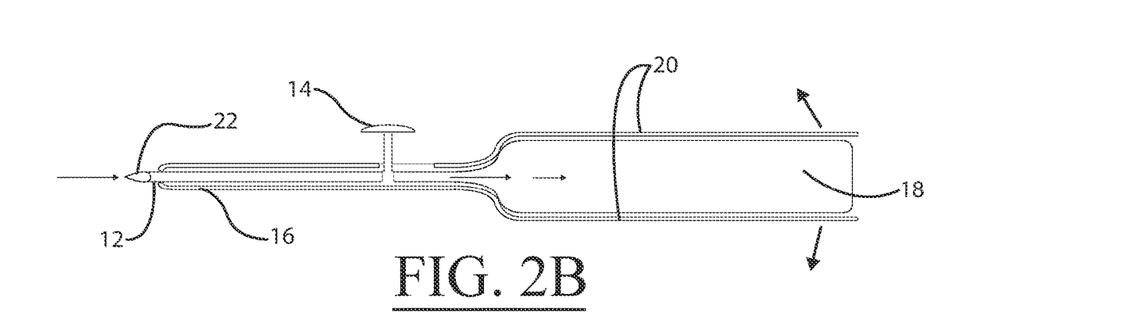
FIG. 2B is another side cross-sectional view of the plungerless aspiration and/or injection device of FIG. 2A, wherein the manner in which the device is used for aspiration is illustrated.

In FIG. 2A, the forked blades 20 of the illustrative plungerless aspiration and/or injection device 10 are shown being compressed by fingers of a user during injection of a fluid disposed in the bulb portion 18 of the device. In FIG. 2B, the forked blades 20 of the illustrative plungerless aspiration and/or injection device 10 are shown being displaced outwardly during aspiration.

Figure 2C:
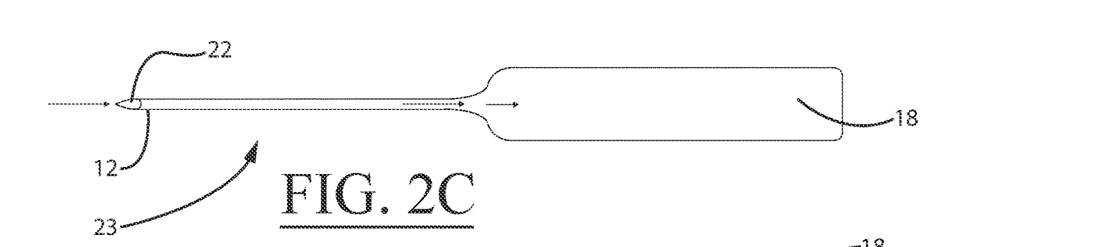
FIG. 2C is a side cross-sectional view of the needle and bulb of the plungerless aspiration and/or injection device of FIG. 2A, wherein the housing has been removed from the device to better illustrate the needle and bulb.
Figure 2D:
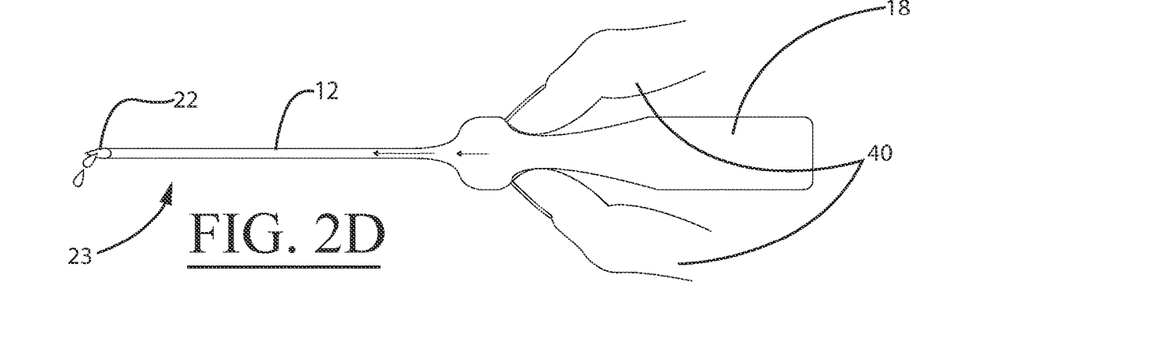
FIG. 2D is another side cross-sectional view of the needle and bulb of the plungerless aspiration and/or injection device of FIG. 2A, wherein the bulb is shown being compressed for active injection.
Figure 2E:
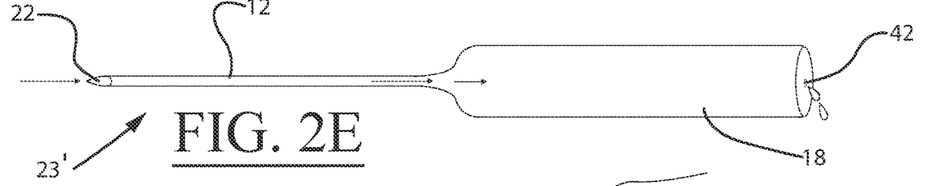
FIG. 2E is a side cross-sectional view of an alternative needle and bulb of the plungerless aspiration and/or injection device of FIG. 2A, where the bulb is provided with a drainage hole therein, and the bulb is shown being used for passive aspiration or drainage.
Figure 2F:
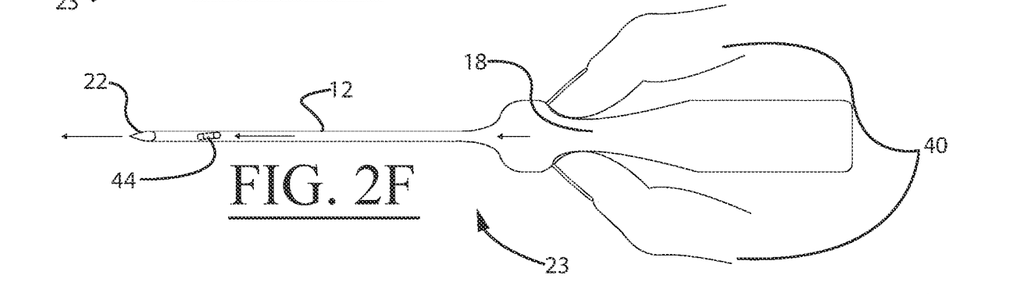
FIG. 2F is still another side cross-sectional view of the needle and bulb of the plungerless aspiration and/or injection device of FIG. 2A, wherein the bulb is shown being compressed for implantation of an implant.
Figure 2G:
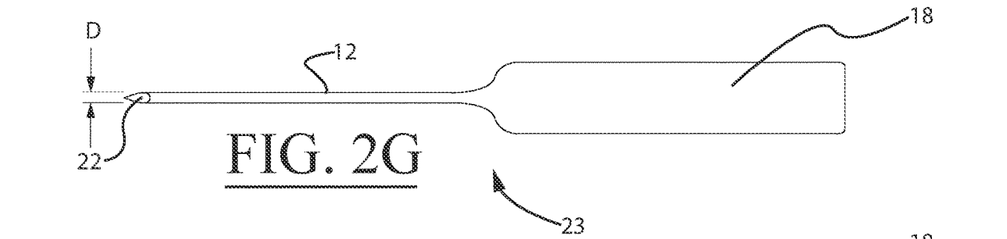
FIG. 2G is yet another side cross-sectional view of the needle and bulb of the plungerless aspiration and/or injection device of FIG. 2A.
Figure 2H:
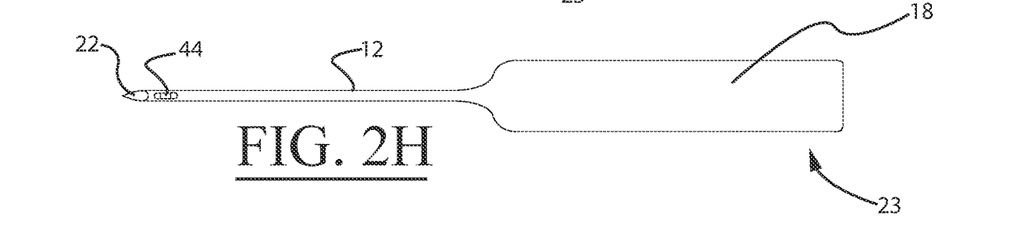
FIG. 2H is still another side cross-sectional view of the needle and bulb of the plungerless aspiration and/or injection device of FIG. 2A, wherein an implant is illustrated in the needle of the device.

The internal portion 23 of the illustrative plungerless aspiration and/or injection device 10 without the housing 16 is depicted in FIG. 2C. As shown in this figure, the internal portion 23 of the illustrative device 10 includes the needle portion 12 and the bulb portion 18. FIG. 2G depicts a view of the internal portion 23 of the illustrative device 10 similar to FIG. 2C, except that the needle diameter D of the needle portion 12 is labeled. In FIG. 2D, the bulb portion 18 of the internal portion 23 of the illustrative device 10 is shown being compressed by fingers 40 of a user during injection of a fluid. In FIG. 2E, an alternative embodiment of the internal portion 23' of the illustrative device 10, which has a drainage hole 42 disposed in the bulb portion 18, is shown being used for passive aspiration or drainage. In FIG. 2F, the bulb portion 18 of the internal portion 23 of the illustrative device 10 is shown being compressed by fingers 40 of a user during the implantation of an implant 44. FIG. 2H depicts a view of the internal portion 23 similar to FIG. 2F, except that the implant 44 is illustrated in the needle portion 12 prior to being injected when the bulb portion 18 is undeformed.

Figure 1D:
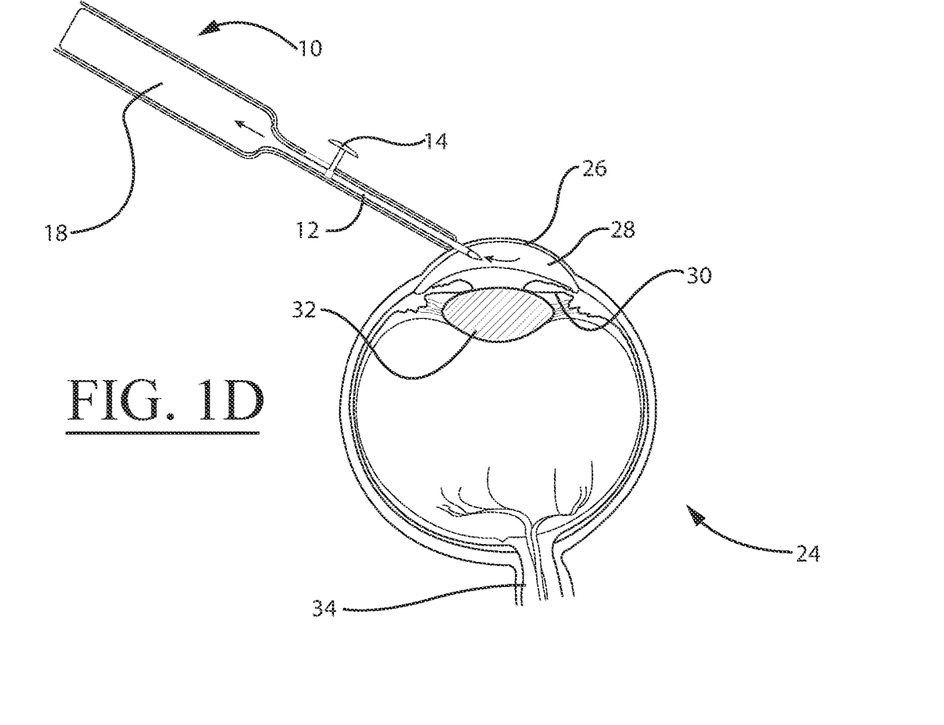
FIG. 1D is a side cross-sectional view of an eye, according to an illustrative embodiment of the invention, wherein the plungerless aspiration and/or injection device of FIG. 1A is being used to aspirate aqueous fluid from the anterior chamber of the eye.
Figure 1E:
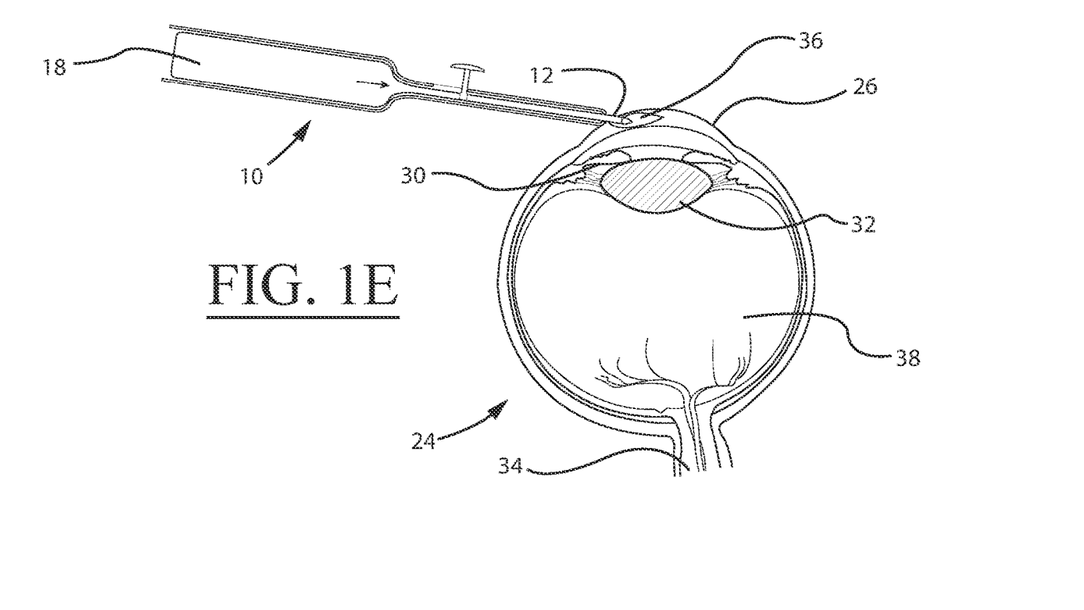
FIG. 1E is a side cross-sectional view of an eye, according to an illustrative embodiment of the invention, wherein the plungerless aspiration and/or injection device of FIG. 1A is being used for intracorneal cavity injection.

In FIG. 1D, an exemplary manner in which an aqueous fluid may be aspirated from the anterior chamber 28 behind the cornea 26 of an eye 24 using the device 10 is illustrated. The eye 24, as illustrated in FIG. 1D, further includes an iris 30, a lens 32, and an optic nerve 34. In FIG. 1E, an exemplary manner in which a substance may be injected into an intracorneal cavity 36 of an eye 24 using the device 10 is illustrated. The eye 24, as illustrated in FIG. 1E, further includes an iris 30, a lens 32, an optic nerve 34, and a vitreous cavity 38.

Figure 3A:
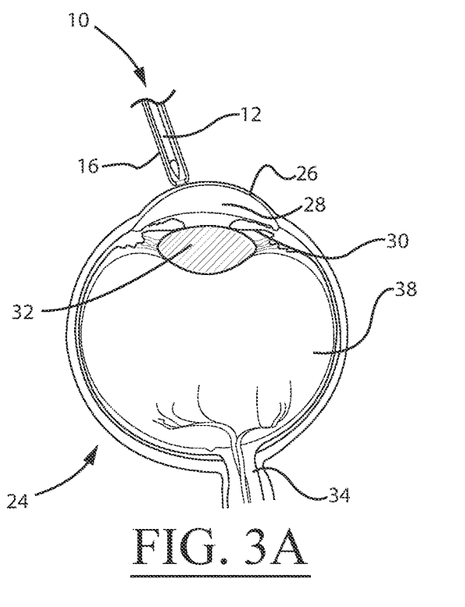
FIG. 3A is a side cross-sectional view of an eye, according to an illustrative embodiment of the invention, wherein the needle tip of the plungerless aspiration and/or injection device has not yet penetrated the cornea of the eye.
Figure 3B:
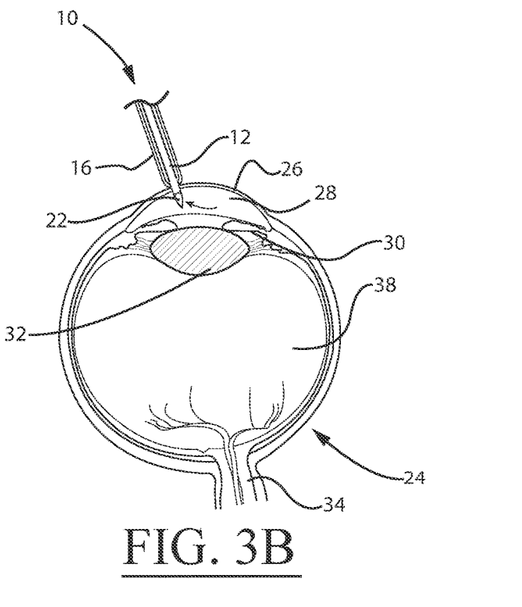
FIG. 3B is another side cross-sectional view of the eye of FIG. 3A, wherein the needle tip of the plungerless aspiration and/or injection device has penetrated the cornea of the eye so that aqueous fluid is able to be aspirated from the anterior chamber of the eye.

In FIGS. 3A and 3B, another exemplary manner in which an aqueous fluid may be aspirated from the anterior chamber 28 behind the cornea 26 of an eye 24 is illustrated. More specifically, FIG. 3A depicts the tip of the plungerless aspiration and/or injection device 10 proximate to the surface of the cornea 26 while the needle portion 12 of the device 10 is still retracted in the housing 16 of the device 10. FIG. 3B depicts the needle portion 12 of the device 10 inserted into the cornea 26, and aqueous fluid being aspirated from the anterior chamber 28 of the eye 24. The eye 24, as illustrated in FIGS. 3A and 3B, further includes an iris 30, a lens 32, an optic nerve 34, and a vitreous cavity 38.

Figures 3C, 3D:
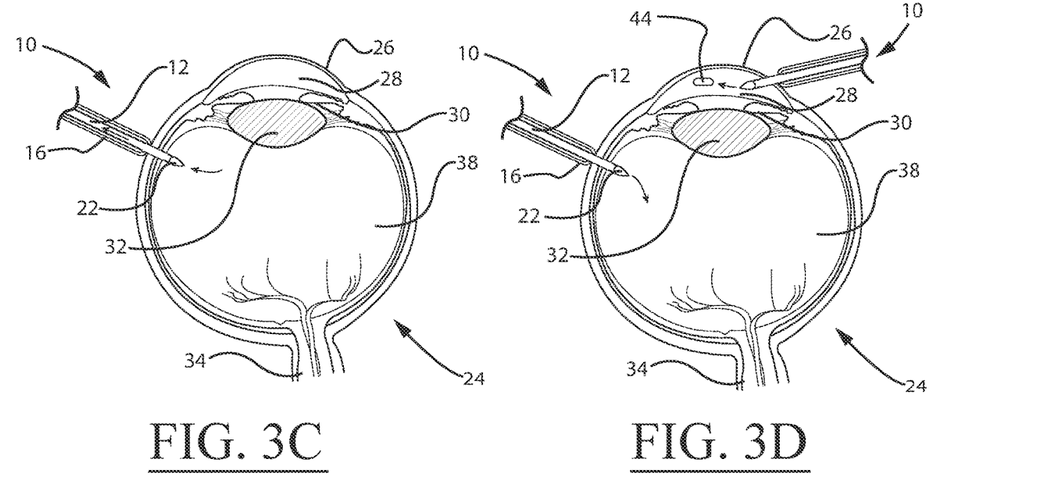
FIG. 3C is yet another side cross-sectional view of an eye, wherein the needle tip of the plungerless aspiration and/or injection device has penetrated the side of the eye so that vitreous fluid is able to be aspirated from the vitreous cavity of the eye.
FIG. 3D is still another side cross-sectional view of an eye, wherein the plungerless aspiration and/or injection device is shown being used for injection or implantation in the anterior chamber of the eye, and the device is additionally shown being used for injection or implantation in the vitreous cavity of the eye.

In FIG. 3C, an exemplary manner in which vitreous humour may be aspirated from the vitreous cavity 38 of an eye 24 using the device 10 is illustrated. In FIG. 3D, an exemplary manner in which a fluid or implant may be injected into the vitreous cavity 38 of an eye 24 using the device 10 is illustrated. Also, in FIG. 3D, another device 10 is shown being used to inject a fluid or implant 44 in the anterior chamber 28 of the eye 24. The eye 24, as illustrated in FIGS. 3C and 3D, further includes a cornea 26, an iris 30, a lens 32, an optic nerve 34, and a vitreous cavity 38.

Figure 3E:
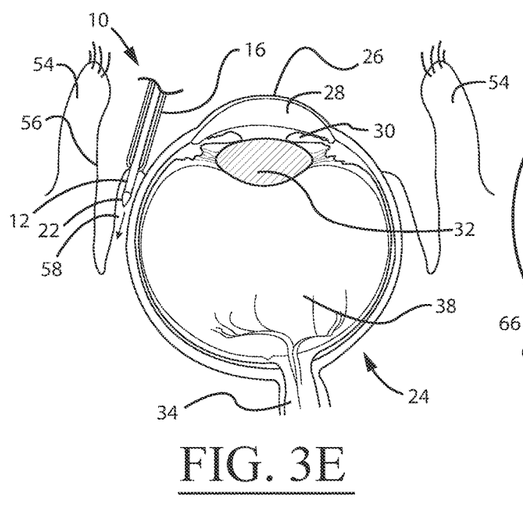
FIG. 3E is yet another side cross-sectional view of an eye, wherein the plungerless aspiration and/or injection device is shown being used for injection or implantation in the sub-conjunctival space of the eye.

In FIG. 3E, an exemplary manner in which a fluidic substance or implant may be injected into the subconjunctival space 58 of an eye 24 using the device 10 is illustrated. The eye 24, as illustrated in FIG. 3E, includes a cornea 26, an anterior chamber 28, iris 30, a lens 32, an optic nerve 34, a vitreous cavity 38, lids 54, and conjunctiva 56.

Figure 3F:
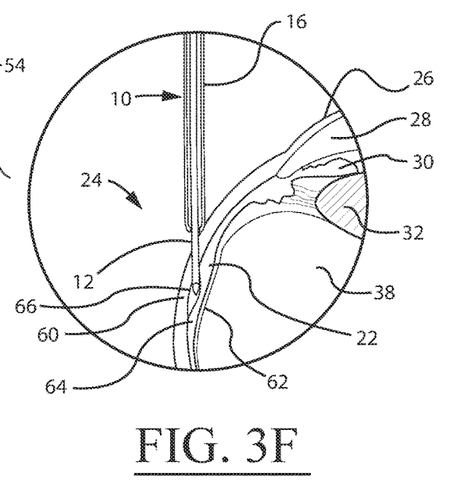
FIG. 3F is still another side cross-sectional view of an eye, wherein the plungerless aspiration and/or injection device is shown being used for injection or implantation in the suprachoroidal space of the eye.

In FIG. 3F, an exemplary manner in which a fluidic substance or implant may be injected into the suprachoroidal space 66 of an eye 24 using the device 10 is illustrated. The device 10 could also be used in a similar manner for aspiration from the suprachoroidal space 66. The eye 24, as illustrated in FIG. 3F, includes a cornea 26, an anterior chamber 28, iris 30, a lens 32, a vitreous cavity 38, a sclera 60, retina 62, and choroid 64.

Figure 3G:
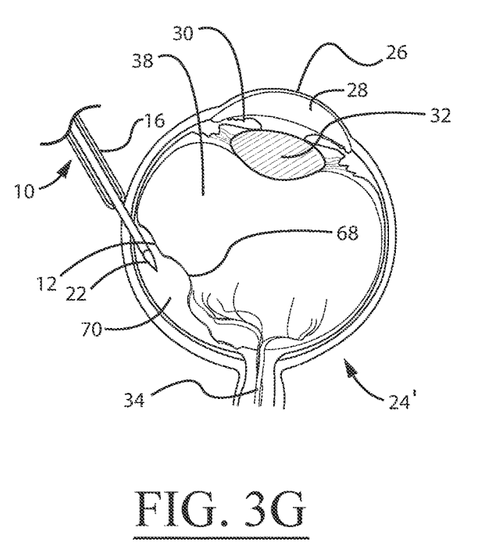
FIG. 3G is yet another side cross-sectional view of an eye, wherein the plungerless aspiration and/or injection device is shown being used for injection or implantation in the subretinal space of the eye.

In FIG. 3G, the eye 24' with cornea 26, anterior chamber 28, iris 30, a lens 32, optic nerve 34, and vitreous cavity 38 has a detached retina 68 that produces a subretinal space 70. The plungerless aspiration and/or injection device 10 may be used to aspirate a fluid from the subretinal space 70 during a medical procedure performed to reattach the retina 68.

Figure 3H:
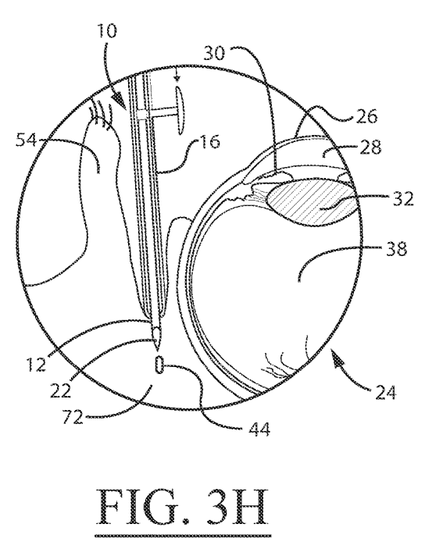
FIG. 3H is yet another side cross-sectional view of an eye, wherein the plungerless aspiration and/or injection device is shown being used for injection or implantation in the retrobulbar space of the eye.

In FIG. 3H, an exemplary manner in which a fluidic substance or implant 44 may be injected into the retrobulbar space 72 of an eye 24 using the device 10 is illustrated. The eye 24, as illustrated in FIG. 3H, includes a cornea 26, anterior chamber 28, iris 30, a lens 32, a vitreous cavity 38, and lid 54.

In one embodiment, the injection is done by actively pressing gently over the flexible spatula and the bulb inside it (refer to FIGS. 2A-2H).

In one embodiment, the needle is pushed in the tissue with the index finger moving the knob located in a slot in the external housing and while the needle is inside the cavity, by releasing slowly the bulb's semi-elastic body expanding automatically and aspirating gradually a small volume of the liquid from the fluid containing cavity, so that it can subsequently be analyzed outside the body using known diagnostic tools such spectrometer, microscope, staining for recognition of various bacteria, fungi, parasites, or viruses, or mass-spectroscopy, PCR, Raman spectroscopy or surface-enhanced Raman spectroscopy technique, enzyme-linked immunosorbent assay (ELISA) test strips, dot blots, solutions on slides, etc. In one embodiment, the biological fluid is anterior chamber fluid and the detection reagent detects a cytokine, etc.

In one embodiment, under normal conditions, the needle tip is retracted and inside the outer metallic, plastic, or glass tube housing, etc. This permits positioning of the instrument with its dull tip end of outer housing to be moved over the tissue surface or inside the tissue and to select a desired location without scratching or cutting the sensitive tissue surface, such as the cornea, skin, mucosa, or choroid, etc.

In one embodiment, the injector carries functionalized antibody-coated nanoparticles with pluralities of nanoparticles conjugated with checkpoint inhibitors and oncolytic viruses to be injected inside a tumor to release the medication as a response to external energy, such as laser, alternating magnetic field, or a focused ultrasound, to treat an external or internal tumor, such as melanomas or precancerous melanoma inside the eye or conjunctiva, lid tumors, breast cancer, prostate cancer, skin tumors, such as squamous cancer or basal cell cancer of the skin.

In one embodiment, the needle can be moved forward or backward by moving a knob connected to the inner needle forward or backward, since the silicone bulb is connected to the needle's end, but is elastic and not fixed to its housing, it can also travel inside the housing forward or backward by the same exposed knob (see FIGS. 1A-1E and FIGS. 2A-2B).

In one embodiment, the needle can be any size with the lengths of 1 mm to 100 mm or more.

In one embodiment, the needle has a diameter of 0.001 mm to 1 mm or more.

In one embodiment, the bulb reservoir by its connection to outside is filled with the air, gas, etc.

In one embodiment, the bulb is filled with a liquid solution or emulsion.

In one embodiment, the bulb is filled with an emulsion containing nanoparticles, microparticles, or larger particles.

In one embodiment, the bulb reservoir contains a viscoelastic material.

In another embodiment, the viscoelastic contains medication or a photosensitizer, such as riboflavin or Porphyrin derivatives, methylene blue or indium, platinum, rhodium plus albumin, eosin, rose Bengal, phthalocyanines, carotenoids, semiconductor nanoparticles, etc. that is activated under ultraviolet (UV) or another radiation to crosslink proteins of an organism.

In one embodiment, the injector is filled with a photosensitizer and an antibiotic, an antifungal, an antiviral, an anticancer medication, anti-parasites, etc.

In one embodiment, the injector is filled with functionalized thermosensitive nanoparticles, such as gold, iron oxide, carbon nanotubes, or thermosensitive polymers, such as liposomes, solid lipids, micelles, nanobubbles, etc. to carry medications in the form of slow release compounds and release the medication after administration.

In one embodiment, the injector carries functionalized antibody-coated nanoparticles with pluralities of nanoparticles conjugated with checkpoint inhibitors and oncolytic viruses to be injected inside a tumor to release the medication as a response to external energy, such as a laser, alternating magnetic field, or a focused ultrasound, to treat an external or internal tumor, such as melanomas or precancerous melanoma, inside the eye or conjunctival or lid tumors, breast cancer, prostate cancer, skin tumors such as squamous cancer or basal cell cancer of the skin.

In one embodiment, the fluid is a viscoelastic material and contains a medication in form of an emulsion containing nanoparticles or micro-particles having a diameter of 1-1000 nm.

In one embodiment, the fluid is a viscoelastic material (e.g., hyaluronic acid or 0.01-1% or more).

In one embodiment, the viscoelastic material is made from another compound.

In another embodiment, the viscoelastic material contains a medication in the form of polymeric slow release nanoparticles or micro-particles of 1-1000 microns or more.

In one embodiment, the polymeric slow release nanoparticles or micro-particles or the implant injected to release medication is made from liposomes, micelles, nano- and micro-particulates of polylactic, polycyclic acid, or in combination with PGLA or porous silicone, nanoparticles of hydrogel, or polyesters, such as polycaprolactone, or other compounds such as chitosan, solid lipids, collagen, alginate dendrimers, metallic nanoparticles such as gold tubes filled with polymeric medications, etc.

In one embodiment, the nanoparticles can be functionalized to attach to certain cells, organisms, bacteria, etc.

In one embodiment, the viscoelastic material carries with it an implant with a diameter of 0.02-2 mm or more.

In one embodiment, the implant can have a length of 0.01-5 mm or more.

In one embodiment, the inner tube is filled with a polymeric drug delivery implant with a diameter of 20-1000 microns and a length of 0.02-100 mm or more as needed.

In one embodiment, the drug or fluid administration, etc. does not require an incision to be made in the tissue (e.g., with a knife, etc.), but the drug or the fluid is administered with the needle's sharp end, which does not require an incision for injection or a suture for its closure.

In one embodiment, the injection is done preferably in an angulated direction to the surface of the tissue that permits the tissue around the injection to close like a valve by the tissue pressure or increased pressure inside the tissue or the cavity after the injection preventing expulsion of the medication or the implant.

In one embodiment, the housing of the needle is positioned over the desired area, then the sharp needle's tip is slowly or gradually moved forward inside the tissue under observation to see the needle tip (e.g., inside the corneal pocket or inside the anterior chamber, etc.) by moving the instrument's knob forward to the desired distance and a desired direction in the tissue of the cavity, then compressing the medication-filled elastic bulb reservoir to release the medication under the observation of the needle's tip in the desired place (refer to FIGS. 2A-2I and FIGS. 3A-3H).

In one embodiment, the housing of the needle is positioned over the desired area, then the sharp needle tip is slowly or gradually moved forward inside the tissue under observation to see the needle tip by moving the instrument's knob forward to the desired distance and desired direction in the tissue or inside the cavity, then compressing the elastic bulb through the elastic forked housing over the bulb. The elastic thin-walled fork over the bulb provides a more controllable pressure to the bulb filled with the medication, etc. to be compressed between the thumb and index finger to slowly release the medication in the desired area or stop at a desired time (see FIGS. 2A, 2B, 2D, and 2F).

In one embodiment, the housing of the needle is positioned over the desired area, then the sharp needle tip is moved slowly or gradually forward inside the tissue under observation to see the needle tip by moving the instrument the knob forward to a desired distance and desired direction in the tissue of the cavity while the bulb is compressed, then the compression of the bulb is released slowly to aspirate fluidic biopsy to a desired volume, the biopsy fluid for subsequent analysis as described (refer to FIGS. 2C and 2E). In one embodiment, the sharp tip of the needle is used inside the tissue, e.g., inside the cornea after femtosecond laser application or a Small Incision Lenticule Extraction (SMILE) procedure to dissect the bridges of the tissue with ease.

In one embodiment, the instrument is equipped with a graded flexible guard that indicates how much fluid or medication is injected in a cavity (e.g., vitreous cavity, in the anterior chamber, under the conjunctival, inside the vitreous cavity, in the suprachoroidal space, under the retina, or anywhere else—see FIG. 2I and FIGS. 3A-3H).

Figure 2I:
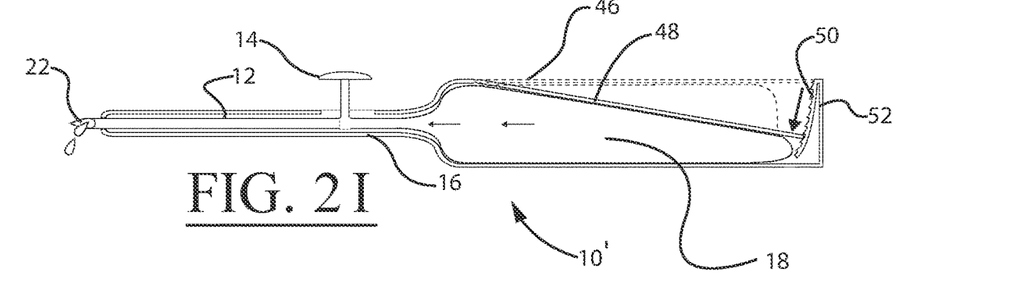
FIG. 2I is a side cross-sectional view of a plungerless aspiration and/or injection device, according to yet another illustrative embodiment of the invention, wherein the bulb of the device is incrementally compressed using a flexible angulated step ladder-like structure.

In one alternative embodiment, as shown in FIG. 2I, by pressing the flexible guard 46 over the bulb 18, a fluid is injected using the plungerless aspiration and/or injection device 10'. In this alternative embodiment, the housing 16 is also equipped with a flexible step ladder stopper 50 either as a rectangular plate or a ring-shaped plate with deep grooves, by pressing one of the forked blades 48 of the housing 16, it falls inside first groove indicating, e.g., 0.05 ml of the fluid is expelled out while making a clicking sound. In one embodiment, one can build the stopper so that each step (groove) would indicate how much more fluid volume is injected inside a cavity from 0.05 to 0.5 ml to 0.1 ml-2.05 ml, etc. as needed precisely (refer to FIG. 2I).

As shown in the alternative embodiment of FIG. 2I, to inject a predetermined amount of a fluid, a user presses the flexible guard 46 over the bulb 18 until the proximal end of the forked blade or pivotable lever 48 seats within one of the grooves in the angulated stepped internal wall 50 of the plungerless aspiration and/or injection device 10', wherein the groove corresponds to a predetermined amount of fluid being discharged from the device 10'. In FIG. 2I, it can be seen that the proximal end of the device 10' is closed by an end cap 52, which is attached to the angulated stepped internal wall 50.

In one embodiment, the needle is inserted inside the tissue or a cavity and the medication, fluid, gas or implant is expelled out by simply applying pressure to the bulb.

In one embodiment, the instrument can be used as a passive system for collection of fluid biopsy from the blood or a body cavity by creating a small hole in the wall of the bulb to release fluid from the body cavity through the needle to the silicone bulb to outside where it can be collected as desired (refer to FIG. 2E).

In one embodiment, a silicone tube is connected to the needle and the external end is connected to an elastic silicone tube to drain the fluid out of the eye cavity in a passive way that can be clamped at any time as known in the art.

In one embodiment, the device permits removal of a small amount of fluid of 0.1 microliters to milliliter, etc. as needed for the analysis either in bacterial, fungal, viruses, parasites, etc. infection, or malaria detection, circulating tumor cells, exosomes, micro-RNS, micro-DNA, antibodies indicating one or other disease process in the eye fluid or elsewhere in a body cavity.

In one embodiment, the needle is inserted in the suprachoroidal space while a thin flexible metallic wire is pushed through it to drain fluid of a pigment epithelial detachment, by inserting the wire from the back into a pigment epithelial detachment space and draining passively the fluid in the choroidal space in the pigment epithelial detachment (see FIG. 3F).

In one embodiment, the silicone bulb can be injected with the medication in liquid or emulsion form or an implant form that can pass through the wall diameter of the needle prior to release of the medication or implant in the eye cavity, corneal cavity, subconjunctival space in the lens capsule after cataract extraction in the lens capsule, or in the sub-retinal space or in the choroid.

In one embodiment, the instrument's needle can be inserted in any place in the eye (refer to FIGS. 3A-3H) or outside the eye (e.g., in the joints, mouth, bladder, vagina, nose, ear, etc., cerebrospinal fluid, etc. to take either a fluid biopsy or injected medication).

In one embodiment, the flexible bulb is used to drop the medication as a drop, or spray the liquid medication of emulsion over or inside a body cavity or over the cornea or under the lid or over the conjunctiva, or over a body's mucosa by compressing rapidly the flexible tail of the instrument with the bulb reservoir to spread the medication in the cavity.

In one embodiment, the medications that are administered using this instrument are steroids, anti-inflammatory agents, NSAIDs, Rock inhibitors, integrin inhibitors, GSK inhibitors alone or in combination in slow release nanoparticle polymers, such as polylactic or glycolic acid, micelles, liposomes, porous silicon, or polyester, and is administered precisely to release the medication in the cornea or inside a body tissue or cavity for a long time after implantation.

In one embodiment, the medications that are administered using this instrument are anti-inflammatory agents, such as Rock inhibitors, GSK inhibitors, integrin inhibitors, alone or in combination with immunosuppressants such as cyclosporine, Mycophenolic acid, ascomycin, metalloproteinase inhibitors, such as doxycycline, tetracycline, etc. or low molecular weight heparin, alone or in combination in slow release nanoparticle or microparticle polymers, such as polylactic or glycolic acid, micelles, liposomes, porous silicon, or polyester to release the medication in the cornea or inside a body tissue or cavity for a long time after implantation.

In one embodiment, the unit can be prefilled with specific non-toxic doses of antibiotics, antivirals, anti-parasites, anti-fungals, or antivirals, etc. in a solution or emulsion of nanoparticles for slow release of the medication.

In one embodiment, the disease process involves the cornea, glaucoma, dry eye, uveitis, retinal detachment, refractive surgery and corneal implantation, optic nerve inflammation, retinitis pigmentosa, diabetic retinopathy, age-related macular degeneration wet or dry form, glaucoma, scleritis and the medication is injected in the cavity or inside the tissue as shown in FIG. 3.

In one embodiment, the instrument can be made sterile with pre-filled medication as a disposable unit to deliver the medication to the quantity/volume as needed.

In one embodiment, the unit can have one or multiple medications, packaged sterile with pre-filled medications as a disposable unit for single use on a patient.

In another embodiment, the unit is sterilized and packaged, and is used for aspiration of a liquid biopsy as a disposable unit for single use on a patient.

Any of the features, attributes, or steps of the above described embodiments and variations can be used in combination with any of the other features, attributes, and steps of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A plungerless aspiration and/or injection device, comprising:
   a housing;
   a needle portion disposed in the housing, the needle portion configured to be selectively retracted and extended by a user, the needle portion comprising a needle tip configured to be inserted into tissue of a patient for aspiration, injection, and/or implantation; and
   a bulb portion disposed in the housing, the bulb portion defining a fluid containing cavity that is fluidly coupled to the needle portion, and the bulb portion being elastically deformable so that the user is able to perform the aspiration, the injection, and/or the implantation on the patient by manipulating the bulb portion.

2. The plungerless aspiration and/or injection device according to claim 1, further comprising a knob for manipulating the needle portion, the knob being slidably disposed within a slot of the housing;
   wherein, when the knob is moved in a first direction by the user, the needle portion is retracted into the housing; and
   wherein, when the knob is moved in a second direction by the user, the needle portion is extended out of the housing, the second direction being opposite to the first direction.

3. The plungerless aspiration and/or injection device according to claim 2, wherein the bulb portion is connected to the needle portion such that the bulb portion is displaced with the needle portion when the knob is moved in the first direction or second direction by the user.

4. The plungerless aspiration and/or injection device according to claim 1, wherein the housing comprises elastically deformable forked blades disposed over the bulb, the elastically deformable forked blades configured to be depressed by the user between a thumb and index finger of the user so as to more controllably regulate a flow of fluid out of, or into the needle tip.

5. The plungerless aspiration and/or injection device according to claim 4, wherein the housing further comprises a plate member with a plurality of grooves disposed therein, and at least one of the elastically deformable forked blades is configured to engage with respective ones of the plurality of grooves in the plate member so as to enable graduated amounts of the fluid to be discharged from the plungerless aspiration and/or injection device.

6. The plungerless aspiration and/or injection device according to claim 1, wherein the needle portion has a 19 gauge to 44 gauge needle diameter.

7. The plungerless aspiration and/or injection device according to claim 1, wherein the needle portion has a diameter between approximately 0.001 millimeters and approximately 1.0 millimeters.

8. The plungerless aspiration and/or injection device according to claim 1, wherein the needle portion has a needle length between approximately 1 millimeters and approximately 100 millimeters.

9. The plungerless aspiration and/or injection device according to claim 1, wherein the bulb portion is formed from a compressible silicone, rubber, or other elastic polymer.

10. The plungerless aspiration and/or injection device according to claim 1, wherein the housing comprises a dull tip end so that, when the needle portion is retracted in the housing, the plungerless aspiration and/or injection device is able to be moved over a surface of the tissue of the patient or inside the tissue of the patient to select a desired penetration location or dissecting location without scratching or cutting the surface of the tissue or the inside of the tissue.

11. The plungerless aspiration and/or injection device according to claim 1, wherein the housing comprises a graded flexible guard that indicates the amount of the fluid or medication that is injected in a body cavity.

12. A method of using a plungerless aspiration and/or injection device, said method comprising the steps of:
   providing a plungerless aspiration and/or injection device that includes:
      a housing;
      a needle portion disposed in the housing, the needle portion configured to be selectively retracted and extended by a user, the needle portion comprising a needle tip configured to be inserted into tissue of a patient for aspiration, injection, and/or implantation; and
      a bulb portion disposed in the housing, the bulb portion defining a fluid containing cavity that is fluidly coupled to the needle portion, and the bulb portion being elastically deformable so that the user is able to perform the aspiration, the injection, and/or the implantation on the patient by manipulating the bulb portion;
   positioning the housing of the plungerless aspiration and/or injection device over a body portion of the patient;
   displacing the needle portion of the plungerless aspiration and/or injection device outward from the housing such that the needle tip penetrates the tissue of the patient; and
   compressing the bulb portion of the plungerless aspiration and/or injection device to either inject a fluid or implant into the tissue of the patient, or to aspirate a fluid biopsy from a body cavity or the tissue of the patient.

13. The method according to claim 12, further comprising the step of:

filling the fluid containing cavity of the bulb portion with a fluid, a medication, an implant, proteins, cells, or genetic components; and wherein the step of compressing the bulb portion further comprises compressing the bulb portion to inject the fluid, the medication, the implant, the proteins, the cells, or the genetic components into the tissue, circulation, or body cavity of the patient.

14. The method according to claim 13, wherein the step of filling the fluid containing cavity of the bulb portion further comprises filling the fluid containing cavity with pluralities of functionalized antibody-coated nanoparticles conjugated with checkpoint inhibitors, oncolytic viruses, viral-like particles, immune stimulators, and/or venoms to be injected inside a tumor or circulation of the patient so as to release checkpoint inhibitors, oncolytic viruses, viral-like particles, immune stimulators, and/or venoms.

15. The method according to claim 14, wherein the checkpoint inhibitors, oncolytic viruses, viral-like particles, immune stimulators, and/or venoms conjugated with the functionalized antibody-coated nanoparticles are released in response to application of external energy, the external energy selected from the group consisting of laser, alternating magnetic field, a focused ultrasound, microwaves, and/or combinations thereof.

16. The method according to claim 13, wherein the step of filling the fluid containing cavity of the bulb portion further comprises filling the fluid containing cavity with an emulsion containing nanoparticles or microparticles, a solvent, and/or a semifluorinated alkane.

17. The method according to claim 13, wherein the step of filling the fluid containing cavity of the bulb portion further comprises filling the fluid containing cavity with a viscoelastic material containing a medication and/or a photosensitizer that is activated using ultraviolet radiation or another type of radiation to crosslink proteins in the tissue of the patient.

18. The method according to claim 17, wherein the photosensitizer is selected from the group consisting of riboflavin, porphyrin derivatives, indium, platinum, rhodium plus albumin, eosin, rose Bengal, phthalocyanines, methylene blue, carotenoids, and/or combinations thereof.

19. The method according to claim 13, wherein the step of filling the fluid containing cavity of the bulb portion further comprises filling the fluid containing cavity with predetermined non-toxic doses of a medication selected from the group consisting of antibiotics, antivirals, antiparasites, anti-fungals, and/or combinations thereof in a solution or emulsion of slow release polymer nanoparticles or microparticles for slow release of the medication.

20. The method according to claim 12, wherein the step of compressing the bulb portion further comprises compressing the bulb portion to aspirate the fluid biopsy from the body cavity or the tissue of the patient for subsequent analysis.

21. The method according to claim 20, further comprising the step of:

creating a small hole in an outer wall of the bulb portion or penetrating the bulb with a fine needle to aspirate the fluid biopsy from the body cavity or the tissue of the patient through the needle portion, to the bulb portion, and then to outside the plungerless aspiration and/or injection device where the fluid biopsy is collected, so that the plungerless aspiration and/or injection device is able to be used as a passive biopsy collection system.

22. The method according to claim 12, wherein the plungerless aspiration and/or injection device is configured for a single use on a patient; and wherein the method further comprises the step of:

disposing of the plungerless aspiration and/or injection device after injecting the fluid or implant into the tissue of the patient, or aspirating the fluid biopsy from the body cavity or the tissue of the patient.

23. The method according to claim 12, further comprising the steps of:

inserting the needle tip of the needle portion of the plungerless aspiration and/or injection device inside corneal tissue after femtosecond laser application or a Small Incision Lenticule Extraction procedure; and displacing the needle tip of the needle portion inside the corneal tissue so as to dissect bridges of the corneal tissue after the femtosecond laser application or the Small Incision Lenticule Extraction procedure.

\* \* \* \* \*